US012653762B2

(12) United States Patent
Pereira

(10) Patent No.: US 12,653,762 B2
(45) Date of Patent: Jun. 16, 2026

(54) SOLID CLEANSING COMPOSITION PRESENTING CONTROLLED DISINTEGRATION

(71) Applicant: Kenvue Brands LLC, Summit, NJ (US)

(72) Inventor: Aline Pereira, São Jose dos Campos (BR)

(73) Assignee: Kenvue Brands LLC, Summit, NJ (US)

( * ) Notice: Subject to any disclaimer, the term of this patent is extended or adjusted under 35 U.S.C. 154(b) by 832 days.

(21) Appl. No.: 17/365,052

(22) Filed: Jul. 1, 2021

(65) Prior Publication Data

US 2022/0015993 A1      Jan. 20, 2022

Related U.S. Application Data

(60) Provisional application No. 63/051,437, filed on Jul. 14, 2020.

(51) Int. Cl.

| | |
|---|---|
| *C11D 17/00* | (2006.01) |
| *A61K 8/02* | (2006.01) |
| *A61K 8/36* | (2006.01) |
| *A61K 8/46* | (2006.01) |
| *A61K 8/73* | (2006.01) |
| *A61Q 19/10* | (2006.01) |
| *C11D 3/22* | (2006.01) |
| *C11D 3/37* | (2006.01) |

(52) U.S. Cl.
CPC ............ *A61K 8/0233* (2013.01); *A61K 8/361* (2013.01); *A61K 8/463* (2013.01); *A61K 8/466* (2013.01); *A61K 8/732* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 5,703,026 A | 12/1997 | Setser et al. | |
| 6,294,509 B1 | 9/2001 | Meiwa et al. | |
| 6,730,642 B1 | 5/2004 | Aronson et al. | |
| 7,465,691 B1 | 12/2008 | Stremilova et al. | |
| 8,211,841 B2 | 7/2012 | Allef et al. | |
| 8,940,680 B2 | 1/2015 | Bernard et al. | |
| 10,774,290 B2 | 9/2020 | Caparrós | |
| 2002/0123442 A1* | 9/2002 | Pawlikowski | A61Q 15/00 510/141 |
| 2002/0151453 A1 | 10/2002 | Abbas et al. | |
| 2003/0086962 A1* | 5/2003 | Westerfield | A61Q 19/10 424/443 |
| 2004/0116317 A1* | 6/2004 | Burt | C11D 1/835 510/447 |
| 2004/0220063 A1 | 11/2004 | Chappell et al. | |
| 2005/0069514 A1 | 3/2005 | Maleedy | |
| 2005/0288208 A1* | 12/2005 | Keenan | C11D 3/3769 510/439 |
| 2010/0330369 A1* | 12/2010 | Veelaert | A61Q 1/10 427/212 |
| 2018/0148674 A1 | 5/2018 | Khamis et al. | |
| 2019/0201345 A1* | 7/2019 | Fujino | A61K 9/2054 |
| 2020/0140781 A1 | 5/2020 | Harper et al. | |

FOREIGN PATENT DOCUMENTS

| | | |
|---|---|---|
| AU | 2003294948 B2 | 11/2006 |
| CN | 1375002 A | 10/2002 |
| CN | 1633279 A | 8/2009 |
| CN | 101514315 A | 8/2009 |
| EP | 956333 B1 | 4/2003 |
| JP | 2001048746 A | 2/2001 |
| JP | 2016216652 A | 12/2016 |
| RU | 2179954 C1 | 2/2002 |
| RU | 2517128 C2 | 5/2014 |
| WO | 01/21756 A | 3/2001 |
| WO | WO 2017/011774 A | 1/2017 |
| WO | 2020089812 A1 | 5/2020 |
| WO | WO 2020/113484 A1 | 6/2020 |
| WO | WO 2012/091598 A1 | 7/2021 |

OTHER PUBLICATIONS

Camarco et al., "Selecting Superdisintegrants for Orally Disintegrating Tablet Formulations", *Pharmaceutical Technology Supplement*, Excipient Performance, Oct. 2006.
Ferrero et al., "Disintegrating efficiency of croscarmellos sodium in a direct compress formulation", *International Journal of Pharmaceutics* (1997) 147:11-21.
ISP, Polyplasdone®Crospovidone Superdisintegrants for Orally Disintegrating and Chewable Tablets (2009).
Nakama, Chapter 15, Surfactants, in Sakamoto et al., *Cosmetic Science and Technology: Theoretical Principles and Applications* (2017) pp. 231-232.
Nnadi et al., "Environmentally friendly superaborbent polymers for water conservation in agruicultural lands", *Journal of Soil Science and Environmental Management* (Jul. 2011) 2(7):206-211.
International search report and written opinion dated Nov. 4, 2021, for international application PCT/IB2021/055914.
Sutĉgin V.M., Bondaletova L.I. "Himiâ i fizika polimerov" [Polymer Chemistry and Physics], Textbook, Tomsk: Tomsk Polytechnic University (TPU) Publishing House, 2003, 208 pages, p. 142.
Ageev A.A. et al. "Zavisimost' poverhnostnogo natâženiâ vodnyh rastvorov ot stroeniâ molekul poverhnostno-aktivnyh veŝestv i sostava adsorbcionnyh sloev" [Dependence of surface tension of aqueous solutions on the structure of surfactant molecules and the composition of adsorption layers], Bulletin of the Association of Universities for Tourism and Service, 2008, v.2, N. 4, pp. 55-61.

* cited by examiner

*Primary Examiner* — Lorna M Douyon

(57) ABSTRACT

A solid cleansing composition comprising a (I) first and a (II) second phase; wherein the (I) first phase comprises a mixture of ingredients including (a) a solid surfactant, (b) a disintegration agent and (c) a lubricant; the (2) second phase comprising (d) a superabsorbent polymer and (e) a binder.

8 Claims, 2 Drawing Sheets

SOLID CLEANSING COMPOSITION PRESENTING CONTROLLED DISINTEGRATION

CROSS REFERENCE TO RELATED APPLICATIONS

This application claims the benefit of U.S. provisional application 63/051,437 filed on Jul. 14, 2020, the complete disclosure of which is hereby incorporated herein by reference for all purposes.

FIELD OF THE INVENTION

The present invention relates to cleansing compositions. More specifically, the invention relates a solid cleansing composition, and a method of obtaining the same.

BACKGROUND OF THE INVENTION

Cleansing compositions are widely used in our society. They are typically used for bathing, cleansing hands, body and hair in almost all phases of peoples' life, from birth to the elderly ages. Cleansing compositions are also employed to care and hygiene other mammals, including pets.

The most traditional form of cleansing compositions are the soap bars obtained by saponification, a conversion process of fats or oils into soap and alcohol under heating in the presence of aqueous alkali as sodium hydroxide. When obtained by saponification, the resulting cleansing formulation tends to present low pH's which may dis-balance the skin, besides its pH, such formulations tend to remove excessively the lipids from the skin, leading to dryness or discomfort to the users. However, such bars are cheap to obtain and lasts for several cleansing procedures.

Additionally, such bars are easy to be employed, simply rubbing it on the wet skin is sufficient to promote a cleansing lather. Preferentially, soap bars are voluminous thus aiding the consumers in grabbing them during use.

An alternative to saponification derived soap bars, are the cleansing formulations including synthetic surfactants, generally gentler to the skin and not as damaging to the environment. Such formulations are commonly found in liquid viscous presentations. Despite advantageously mild to the skin, those formulas need to be packed on flasks or bottles. Additionally, they are preferentially applied on to the skin by means of sponges in order to promote lathering and avoiding it to be quickly washed. Further preferentially, such bottles include complex dispensing means aiding the user to properly select the right amount of the formulation to be poured on to the sponge or directly to the skin.

Another disadvantage found in liquid cleansing formulations are that they typically include high contents of water, increasing the mass of volume to be transported and stored during their commercialization.

SUMMARY OF THE INVENTION

We have found novel cleansing compositions to overcome some disadvantages found in employing currently available cleansing compositions.

In one first aspect, the invention consists of a solid cleansing composition comprising a (I) first and a (II) second phase; the (I) first phase comprising a mixture of ingredients including (a) a solid surfactant, (b) a disintegration agent and (c) a lubricant; the (II) second phase comprising (d) a superabsorbent polymer and (e) a binder.

In preferential embodiment's of the invention, suitable (a) solid surfactants are Plantapon SUS (Disodium Lauryl Sulfosuccinate), Coliform SLS (sodium lauryl sulfate), or Jordapon (Fatty acids, coco, 2-sulfoethyl esters, sodium salts); suitable (b) disintegration agents are Pregelatinized starch, or Lactose 200 mesh; a suitable (c) lubricant is Magnesium Stearate; suitable (d) superabsorbent polymers are starch grafted superabsorbent polymers (SGSAPs); and a suitable (e) binder is water.

Further accordingly to the invention, the (I) first and (II) second phases are arranged in layers adjacently to each other.

In a second aspect of the invention, the solid composition is a single use solid cleansing composition, when exposed to liquids the (I) first phase will produce lather, while the (II) second phase will swell. The solid composition will remain integrated during use for a limited amount of time, once reached its limits it disintegrates.

DETAILED DESCRIPTION OF THE INVENTION

Figure 1:
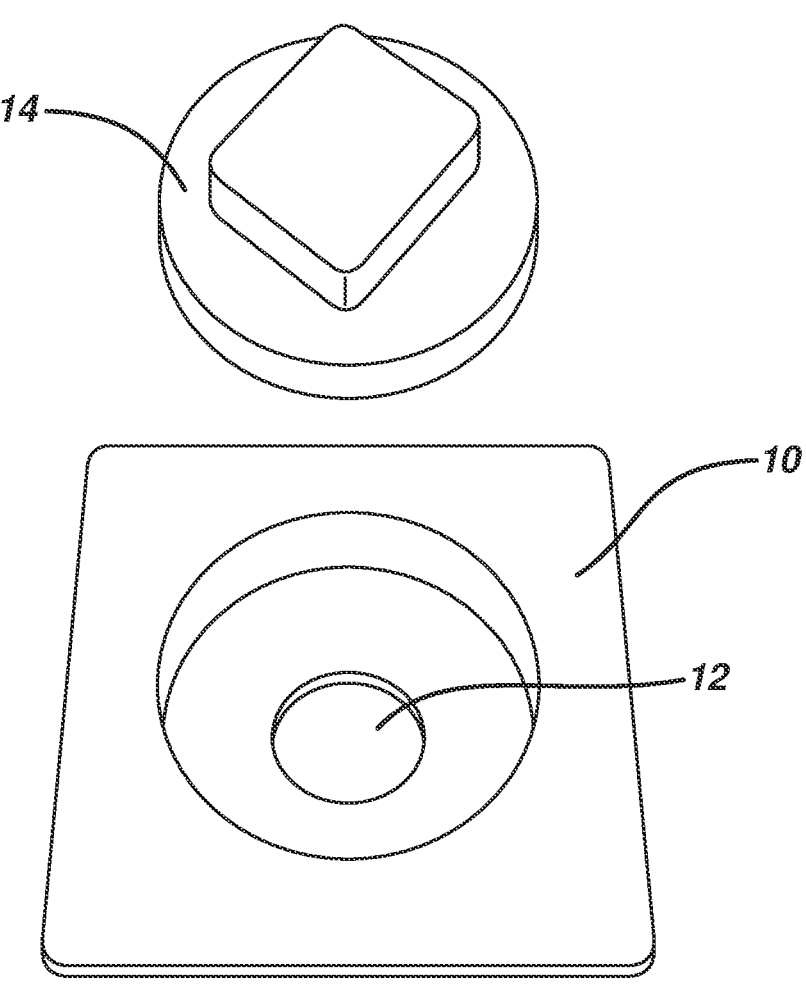
FIG. 1 depicts a mold used to obtaining the samples herein described.

In one first aspect, the invention consists of a solid cleansing composition comprising a (I) first and a (II) second phase; the (I) first phase comprising a mixture of ingredients including (a) a solid surfactant, (b) a disintegration agent and (c) a lubricant; the (II) second phase comprising (d) a superabsorbent polymer and (e) a binder.

In preferential embodiment's of the invention, suitable (a) solid surfactants are Plantapon SUS (Disodium Lauryl Sulfosuccinate), Coliform SLS (sodium lauryl sulfate), or Jordapon (Fatty acids, coco, 2-sulfoethyl esters, sodium salts); suitable (b) disintegration agents are Pregelatinized starch, or Lactose 200 mesh; a suitable (c) lubricant is Magnesium Stearate; suitable (d) superabsorbent polymers are starch grafted superabsorbent polymers (SGSAPs); and a suitable (e) binder is water.

Further accordingly to the invention, the (I) first and (II) second phases are arranged in layers adjacently to each other.

In a second aspect of the invention, the solid composition is a single use solid cleansing composition, when exposed to liquids the (I) first phase will produce lather, while the (II) second phase will swell. The solid composition will remain integrated during use for a sufficient amount of time, once reached its limits it disintegrates.

Surfactants are substances that are called micelles, i.e. chemical substances that create self-assemble molecular cluster in a solution (water or oil phase), and adsorb to the interface between a solution and a different phase (gases/solid). The surfactant must have a chemical structure with two different functional groups named hydrophobic and hydrophilic respectively, with different affinity within the same molecule. Usually the surfactants have both an alkyl chain with 8-22 carbons. This chain is the hydrophobic group, which does not show affinity to water (they are called hydrophobic groups since surfactants are often used in water systems, but when used in lipid systems they are called lipophilic groups). The surfactant molecules also have a functional group named hydrophilic group that has affinity to water. This kind of structure with two opposing functions is known as an amphiphilic structure (see Nakama, Y. "Chapter 15: Surfactants." in Sakamoto, K. et al. *Cosmetic Science and Technology: Theoretical Principles and Applications* (Cambridge, MA, Elsevier Inc., 2017). pp. 231-244). The suitable surfactants to the invention are solid surfactants, as are Plantapon SUS (Disodium Lauryl Sulfosuccinate), Coliform SLS (sodium lauryl sulfate), or Jordapon (Fatty acids, coco, 2-sulfoethyl esters, sodium salts).

As used herein, the term "disintegration agent" and variants there of relate to ingredients that are included in the composition to promote the disintegration of its phase when wet. Besides promoting disintegration, they could also be diluents, so as herein described, the term disintegration agents encompasses the function of fillers. As further discussed, compressibility is an important property to be found in the disintegration included in the solid compositions o the invention. Suitable disintegration agents are starches, as like pregelatinized starch, or Lactose 200 mesh.

The used herein, the term "lubricant" and variants thereof relate to ingredients that promote the proper mixture of the ingredients, particularly promoting the movement of the mixed particles during the manufacture of the composition. According to the present invention, although preferential but not necessary, lubricants assists the movement of the mixed particles, and consequently facilitating the flow of them during the compression step. Accordingly, a suitable lubricant is magnesium stearate.

The superabsorbent polymers (SAPs) are a class of materials that are able to absorb large amounts of water, at least 10 times their own weight in aqueous fluid under moderate pressure. Generally, they consist of a network of polymer chains that are crosslinked to avoid dissolution. Usually there are ionic functional groups along the polymer chains to encourage diffusion of water within the network. Polyacrylate is the most commonly found material in the SAP industry. Superabsorbent polyacrylates are prepared by polymerizing acrylic acid with a crosslinker (see Nnadi, F. and Brave, C. *Environmentally friendly superabsorbent polymers for water conservation in agricultural lands. Journal of Soil Science and Environmental Management*, Vol. 2(7) (July 2011), pp. 206-211).

Preferentially, the superabsorbent polymer included in the cleansing composition of the present invention are starch-grafted superabsorbent polymers (SGSAPs), since they present a higher biodegradability in comparison to regular superabsorbent polymers.

A suitable SGSAP is the starch-based sodium polyacrylate graft polymer named XGF 450, supplied by Corno Cascasdes LLC (Beaverton, Oregon, USA).

Other known SGSAPs are those sold under the names Sanfresh ST-100C, ST100MC, IM-300MC by the company Sanyo Chemical Industries, Water Lock A-240, A-180, B-204, D-223, A-100, C-200, D-223, by the company Grain Processing, FAVOR® max2010 and FAVOR® max2020) from Evonik, among others.

Embodiments of the Invention

Multilayered, single use, solid cleanser product including.
at least one surfactant layer which comprises a solid surfactant (preferably from about 7 to about 47 wt-%, more preferably about 17 to about 37 wt-% of the surfactant layer), a disintegration agent (preferably from about 50 to about 90 wt-%, and more preferably, about 60 to about 80 wt-% of the surfactant layer), and optionally a lubricant (preferably less than about 5 wt-% of the said surfactant layer, more preferably from 1 wt-% to 5 wt-% even more preferably from 2 wt-% to 5 wt-%) and
at least one structural layer which comprises a structural agent (SAP), a binder,
and wherein said solid cleanser product is disintegrable as described above.

Multilayered, single use, solid cleanser product described above,
wherein the solid surfactant is a mild surfactant selected from the group consisting of alky sulfosuccinate, alkyl sulfate, fatty acid sulfo esters, preferably Disodium Lauryl Sulfosuccinate, sodium lauryl sulfate, or Fatty acids coco 2-sulfoethyl esters sodium salts.

Multilayered, single use, solid cleanser product described above,
wherein said disintegration agent is selected in a list comprising carboxymethylcellulose, Sodium starch glycolate, Polyvinyl pyrrolidone, pregelatinized starch, or Lactose; preferably selected among pregelatinized starch, or Lactose 200 mesh.

Multilayered, single use, solid cleanser product described above,
wherein said solid cleanser product includes a lubricant, and said lubricant is magnesium stearate.

Multilayered, single use, solid cleanser product described above,
wherein said structural agent is a superabsorbent polymer (preferably starch-based sodium polyacrylate grafted polymer and preferably comprises at least about 50 wt-% of the said structural layer and more preferably from 55 wt-% to 80 wt-% of the said structural layer)

Multilayered, single use, solid cleanser product described above,
wherein said binder is selected from the group consisting of water, alcohol, glycerin, or glycero 1 (preferably said binder is water and preferably comprises less than about 50 wt-% of the said structural layer and more preferably from 20 wt-% to 45 wt-% of the said structural layer).

Multilayered, single use, solid cleanser product described above,
wherein said solid surfactant, disintegration agent, lubricant and structural agent, are biodegradable.

Multilayered, single use, solid cleanser product described above,
comprising one surfactant layer, and one structural layer.

Multilayered, single use, solid cleanser product described above,
comprising one surfactant layer disposed between two structural layers.

Multilayered, single use, solid cleanser product described above,
comprising one structural layer disposed between two surfactant layers.

Multilayered, single use, solid cleanser product described above,
wherein said solid cleanser product comprises from 60 wt-% to 80 wt-% of said surfactant layer, preferably 65 wt-% to 75 wt-%.

Multilayered, single use, solid cleanser product described above,
wherein said solid cleanser product comprises from 20 wt-% to 40 wt-% of said structural layer, preferably 25 wt-% to 35 wt-% of said structural layer.

Multilayered, single use, solid cleanser product described above,

wherein the layers are directly compressed together, to obtain a tablet.

Process for the manufacture of a multilayered, single use, solid cleanser product, comprising the following steps:

placing at least one surfactant layer which comprises a solid surfactant, a disintegration agent, and optionally a lubricant, and at least one structural layer which comprises a structural agent (SAP), a binder, in contact, compressing the superposed at least two layers to a direct compression force of at least 700 psi for at least one cycle, optionally more than one cycle.

Use of a multilayered, single use, solid cleanser product described above, for a cosmetic application in personal care product.

Multilayered, single use, solid cleanser product described above, wherein the solid cleanser product has a disintegration time comprised between 2 to 15 minutes, produces lather, and said at least one structural layer swells to produce a sponge texture.

While the foregoing descriptions represent exemplary compositions made accordingly of the invention, it will be understood that various additions, modifications and substitutions may be made therein without departing from the spirit and scope of the present invention. The presently disclosed examples are therefore to be considered in all respects as illustrative and not restrictive, the scope of the invention being indicated by the appended claims, and not limited to the foregoing description.

Suitable compositions made for obtaining a first phase of the solid composition of the present invention:

Mixture 4:

| | Function | Mass (g) | w/tw (%) |
|---|---|---|---|
| Pre gelatinized starch | disintegrant | 40 | 64.52 |
| Plantapon SUS | surfactant | 20 | 32.26 |
| Magnesium stearate | lubricant | 2 | 3.23 |
| | total | 62 | 100.00 |

Mixture 5:

| | Function | Mass (g) | w/tw (%) |
|---|---|---|---|
| Lactose 200 mesh | disintegrant | 25 | 69.44 |
| Coliform SLS | surfactant | 10 | 27.78 |
| Magnesium stearate | lubricant | 1 | 2.78 |
| | total | 36 | 100.00 |

Mixture 6:

| | Function | Mass (g) | w/tw (%) |
|---|---|---|---|
| Lactose 200 mesh | disintegrant | 25 | 69.44 |
| Jordapon | surfactant | 10 | 27.78 |
| Magnesium stearate | lubricant | 1 | 2.78 |
| | total | 36 | 100.00 |

6

Suitable compositions made for obtaining a second phase of the solid composition of the present invention:
Second phase:

| | Function | Mass (g) | w/tw (%) |
|---|---|---|---|
| XGF 450 (SGSAP) | SAP | 5 | 62.50 |
| Water | binder | 3 | 37.50 |
| | total | 8 | 100.00 |

EXAMPLES

The following samples were built and labeled 4A, 4B, 5A, 5B, 5C, and 6A, respectively, where:

5A—It included 3 layers; two layers of mixture 5 as the first phase, and a single layer of the second phase composition sandwiched in the middle;

6A—It included 2 layers; a single layer of mixture 6 as the first phase opposed to a single layer of the second phase composition;

4A—It included 2 layers, a single layer of mixture 4 as the first phase opposed to a single layer of the second phase composition;

5B—It included 2 layers, a single layer of mixture 5 as the first phase opposed to a single layer of the second phase composition;

5C—It included 3 layers, two layers of the second phase, and a single layer of mixture 5 sandwiched in the middle; and, 4B—It included 3 layers, two layers of the second phase, and a single layer of mixture 4 sandwiched in the middle.

The samples followed a 1:1 ratio between the first and second phases. Accordingly, as each composition sample weighted substantially 10 g, they included 5 g of the first phase composition, and 5 g of the second phase composition. The embodiments including just two layers, presented their first and second phases laying adjacently on to each other, while those presenting three layers had one of their phase being equally divided in two thinner layers; wherein the other phase was sandwiched between two thinner layers of the divided phase.

Further accordingly, the first and second phase compositions were previously mixed and put aside. The first phase powder ingredients were weighted and added to a plastic bag to be mixed under manual agitation during 1 min. Once prepared, the compositions were placed inside the mold in layers, the sequence of layer deposition following upon the sample configuration, i.e.; bi-layered or sandwiched (three or more layers). The mold 10, as depicted in FIG. 1, has a disc-shaped cavity 12 having dimensions corresponding to the final dimensions of the "coin" shaped compressed product and a plunger 14 coupleable to the ram of a press. The mold 10 was built by a 3D printer in ABS resin (ABS plus—P430 production grade thermoplastic), having an internal diameter of 5 cm, and a thickness/height of 1.5 cm.

Once placed inside the mold, the compositions were compressed by a pneumatic press at a pressure of 750 psi for 5 seconds and repeated 3 times.

The resulting compression turned the powdery compositions in to substantially integrated and solid volumes. More particularly, in "coin" like shaped solid cleansing compositions.

Disintegration Assay

A disintegration assay procedure was developed aimed to simulate the performance of the cleansing composition during use. The solid compositions were then submerged in water at constant shear stresses achieved by water agitation. Parameters like variation in mass and other visually observations like the integrity of the cleansing composition were then evaluated.

Accordingly, a stainless steel sieve, a thermometer, a glass beaker, a magnetic bar and a magnetic stirrer featured with a heater (IKA—model RH Basic) were employed in the disintegration assay described in more detail, below.

The disintegration assay included the following steps:

Step 1: In a glass beaker with a capacity for 1 liter, include 750 mL of conventional tap water;

Step 2: Heat and keep the water temperature to 37° C. under constant stirring of 600 rpm;

Step 3: With the aid of a stainless steel sieve, place the testing sample inside the beaker, being completely under water;

Step 4: At the end of 1 minute, remove the stainless steel sieve from the beaker. Remove water excess by using paper towels;

Step 5: Weight the stainless steel sieve plus the testing sample by using a precision analytical balance previously tared for the stainless steel sieve weight, and record weight;

Step 6: Perform a visual observation of the integrity of the testing sample, and record it by a picture obtained with a photo camera;

Step 7: If still integrated, return the stainless steel sieve plus the prototype to the beaker;

Step 8: Repeat steps 3 to 7 until complete dissolution of the testing sample is observed.

Test Results

When tested accordingly to the disintegration assay, different disintegration properties were observed among the samples, as further and foregoing discussed, differences in integrity lasting time and mass variation until disintegration were observed.

As different mixtures for the first phase were tried but failed to achieve an initial integrity after the compressing step. It is relevant to note here the fact that all tested samples were manual and visually inspected about its integrity, and only the samples found solid and integrated as a unitary piece were tested.

The samples including the mixture 4 as the composition for its first phase are those who last integrated for longer time. Where 15 minutes lasting time for sample 4B, and 13 minutes lasting time for sample 4A were observed.

Accordingly. Sample 4B swelled by augmenting its mass up to 116.8%.

The sample 5C is the one that lasted less, remaining integrated for just 1 minute.

Figure 2:
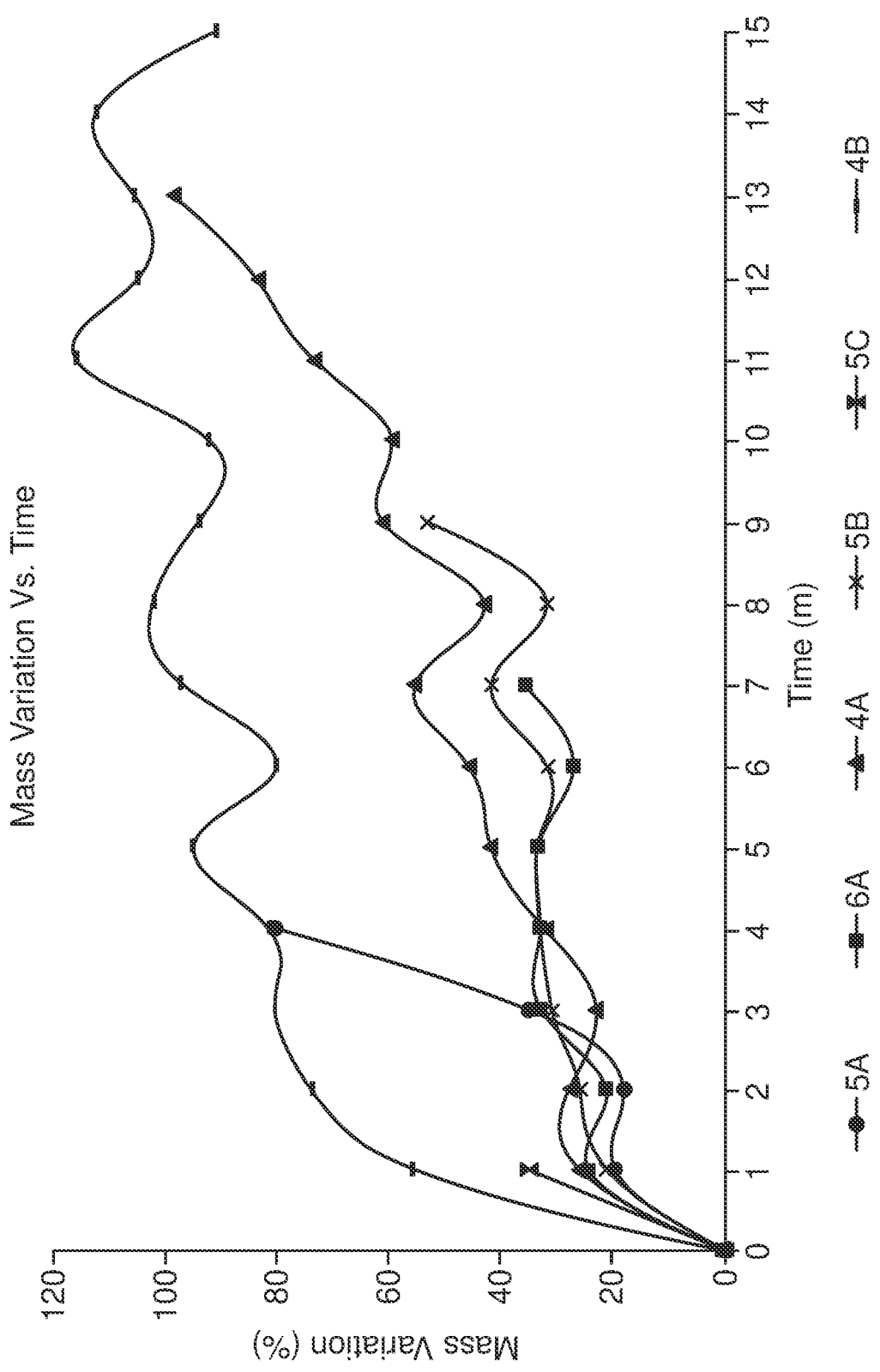
FIG. 2 is a graphic display of the disintegration properties of the tested samples.

As shown in FIG. 2, all samples showed an augmented mass during testing. This is believed to happen because although first phase of each sample disintegrated under agitating water, their second phase, including superabsorbent, augmented by absorbing water.

The sample 6A is the one that swelled less until disintegrating. It swelled by augmenting its mass by up to 33.6%.

Accordingly, depending on some desired functionalities of the solid cleansing composition, different compositions and constructions can be made in order to manage the product disintegration and swelling during use. Large product swelling could be desired for a bathing cleansing, simulating the fell and volume typically known from brand new solid bar of soaps, but avoiding the disadvantages of saponification. A quicker dissolving product might be appreciated for quicker or small cleansing procedures, like washing hands or face.

What is claimed is:

1. A multilayered, single use, solid cleanser personal care product consisting essentially of a solid cleansing composition comprising a (I) first phase and a (II) second phase; wherein the (I) first phase comprises a mixture of ingredients including (a) a solid surfactant, (b) a disintegration agent comprising pregelatinized starch, and (c) a lubricant comprising magnesium stearate; the (2) second phase comprising (d) a superabsorbent polymer selected from the group consisting of starch-grafted superabsorbent polymers and/or mixtures thereof, and (e) a binder comprising water, and wherein the (I) first and (II) second phases are arranged in layers adjacently to each other and wherein the multilayered, single use, solid cleanser personal care product disintegrates during use.

2. The personal care product of claim 1 wherein the (a) solid surfactant is selected from Disodium Lauryl Sulfosuccinate, sodium lauryl sulfate, sodium cocoyl isethionate or their mixtures.

3. The personal care product of claim 1 wherein the (I) first phase is divided in, at least, two layers; wherein the second phase is sandwiched between two layers of the first phase.

4. The personal care product of claim 1 wherein the second phase is divided in, at least, two layers; wherein the first phase is sandwiched between two layers of the second phase.

5. The personal care product of claim 1 wherein the (I) first phase includes from about 50 wt-% to about 90 wt-% of disintegrant, from about 7 wt-% to about 47 wt-% of surfactant, and the lubricant is present in an amount of less than about 5 wt-%.

6. The personal care product of claim 1 wherein the (I) first phase includes from about 60 wt-% to about 80 wt-% of disintegrant, from about 17 wt-% to about 37 wt-% of surfactant, and about 2 wt-% to about 5 wt-% of lubricant.

7. The personal care product of claim 1 wherein the (I) first phase includes about 70 wt-% of disintegrant, 27 wt-% of surfactant, and 3 wt-% of lubricant.

8. The personal care product of claim 1 wherein the mass ratio between the (I) first and (II) second phases is about 1:1.

* * * * *